United States Patent
Kinyon (10) Patent No.: US 9,433,469 B2
(45) Date of Patent: Sep. 6, 2016

(54) PACKAGING FOR ARCUATE ORTHOPEDIC IMPLANTS SUCH AS A SIZE VARYING SERIES OF FEMORAL COMPONENTS FOR ARTIFICIAL KNEE JOINTS

(71) Applicant: PERFECSEAL, INC., Oshkosh, WI (US)

(72) Inventor: Tad R. Kinyon, Elysian, MN (US)

(73) Assignee: Bemis Company, Inc., Neenah, WI (US)

( * ) Notice: Subject to any disclaimer, the term of this patent is extended or adjusted under 35 U.S.C. 154(b) by 0 days.

(21) Appl. No.: 14/391,133

(22) PCT Filed: Apr. 22, 2013

(86) PCT No.: PCT/US2013/037539
§ 371 (c)(1),
(2) Date: Oct. 7, 2014

(87) PCT Pub. No.: WO2013/163064
PCT Pub. Date: Oct. 31, 2013

(65) Prior Publication Data
US 2015/0136625 A1    May 21, 2015

Related U.S. Application Data

(63) Continuation-in-part of application No. 13/453,594, filed on Apr. 23, 2012, now abandoned.

(51) Int. Cl.
*A61C 19/02*    (2006.01)
*A61B 19/02*    (2006.01)
(Continued)

(52) U.S. Cl.
CPC ............. *A61B 19/026* (2013.01); *A61B 50/30* (2016.02); *A61F 2/0095* (2013.01); *A61B 2050/314* (2016.02); *A61F 2/38* (2013.01)

(58) Field of Classification Search
CPC ... B65D 25/10; A61F 2/0095; A61F 19/026; A61C 19/02
USPC ......................................... 206/363, 368, 369
See application file for complete search history.

(56) References Cited

U.S. PATENT DOCUMENTS 4,014,433 A * 3/1977 Cerwin ............ A61B 17/06133
156/182
4,697,703 A * 10/1987 Will ...................... A61F 2/0095
206/363

(Continued)

FOREIGN PATENT DOCUMENTS

JP    2007076503 A    7/2007
WO    2006031162 A1    3/2006

*Primary Examiner* — King M Chu
(74) *Attorney, Agent, or Firm* — Sheena E. Conners (57) ABSTRACT

The present disclosure concerns packaging adapted to accommodate a series of implant components, e.g. femoral components for artificial knee joints, which vary in size but have a common thickness dimension. The packaging is designed to provide a clearance between its internal parts which approximates this common thickness dimension but is also able to accommodate variations in the other dimensions of the implant components. In a convenient approach, a base portion is provided which has a vertical projection with a top surface adapted to support a portion of the inner surface of the major arch of the components of said series. It is mated with a second structural member which has an arcurate surface whose contour approximates a portion of the outside surface of the major arch of the components in this series. Means are provided for holding it in a fixed special relationship with said base portion.

24 Claims, 10 Drawing Sheets

(51) Int. Cl.
*A61F 2/00* (2006.01)
*A61F 2/38* (2006.01)

(56) References Cited

U.S. PATENT DOCUMENTS

| | | |
|---|---|---|
| 5,193,679 A | 3/1993 | White |
| 5,379,895 A | 1/1995 | Foslien |
| 5,392,909 A | 2/1995 | Hackett |
| 5,405,005 A | 4/1995 | White |
| 5,468,526 A * | 11/1995 | Allen ............... A61F 5/445 |
| | | 156/244.11 |
| 5,474,179 A * | 12/1995 | Iosif ............... A61F 5/451 |
| | | 206/363 |
| 5,494,162 A | 2/1996 | Treace et al. |
| 5,772,031 A | 6/1998 | Landis |
| 5,842,567 A | 12/1998 | Rowe et al. |
| 6,012,580 A | 1/2000 | Peters et al. |
| 6,076,876 A | 6/2000 | Letourneau et al. |
| 6,561,805 B2 | 5/2003 | Kumar |
| 7,073,680 B2 | 7/2006 | Boback et al. |
| 7,118,003 B2 | 10/2006 | Sellari et al. |
| 7,316,318 B1 | 1/2008 | Rosten et al. |
| 7,648,030 B2 | 1/2010 | Landis |
| 7,931,148 B2 | 4/2011 | Hansen et al. |
| 8,006,839 B2 * | 8/2011 | Hafner ............... A61F 2/0095 |
| | | 206/363 |
| 2002/0104770 A1 | 8/2002 | Shapeton et al. |
| 2003/0148124 A1 | 8/2003 | Yamada et al. |
| 2005/0051549 A1 * | 3/2005 | Nelson ............... B65D 21/0219 |
| | | 220/23.83 |
| 2007/0034538 A1 * | 2/2007 | Landis ............... A61F 2/0095 |
| | | 206/438 |
| 2007/0295620 A1 | 12/2007 | Collet et al. |
| 2011/0036736 A1 | 2/2011 | Knowlton et al. |
| 2011/0155592 A1 | 6/2011 | Liccardo et al. |

* cited by examiner

PACKAGING FOR ARCUATE ORTHOPEDIC IMPLANTS SUCH AS A SIZE VARYING SERIES OF FEMORAL COMPONENTS FOR ARTIFICIAL KNEE JOINTS

BACKGROUND OF THE INVENTION

The packaging of arcuate orthopedic implants such as the femoral component used in the orthopedic knee arthroplasty procedure has traditionally involved the use of inserts to stabilize the femoral component within the package and these inserts have been tailored to the size of a particular femoral component. Femoral components are currently available in a substantial number of sizes with some manufacturers offering as many as ten sizes in order to better meet the needs of individual patients.

The traditional packaging of sterile medical devices such as implants including femoral components has involved a system of an inner tray within an outer tray. Each tray is typically an open mouthed cavity with a peripheral rim to which a film is adhesively adhered to create a sealed package. The outer tray simply contains the inner tray which in turn contains the medical device, commonly stabilized within the tray with closed cell foam pieces. The pieces of foam are commonly selected to have configurations adapted to the particular device being packaged. Thus in the case of femoral components different pieces of foam are required in progressing across the size range of such components. The two tray system provides some assurance that if the integrity of the outer tray is breached in shipping and handling, the sterility of the packaged medical device is preserved by the inner tray.

This two tray system has some disadvantages. The foam used for stabilization within the inner tray is friable and, particularly with orthopedic implants with roughened surfaces to enhance bonding to living tissue, typically bone, it has been observed to abrade, creating a particulate contaminate. In addition, because the peripheral rim of the inner tray typically carries residual adhesive after the removal of the lid stock, it may not be placed on the surgical tray adjacent to the surgeon implanting the device. Consequently, the medical device must be fully removed from its protective packaging well before its use and is thus exposed to damage and being splashed with bodily fluids and tissue while awaiting implantation.

Thus there are benefits to be gained from a packaging approach in which a single system can be used across the size range of at least a single line of femoral components of a given design or from a single manufacturer. There are further benefits to be obtained from a unitary package which can be removed from an inner tray and placed on a surgical tray thus providing protection for the packaged component until it is used and providing a convenient manner of presenting the component to the surgical team.

SUMMARY OF THE INVENTION

The present invention involves a package which is adapted to securely hold arcuate orthopedic implants such as any of a series of femoral components of artificial knee joints which have an approximate common thickness dimension but vary in size. This package is configured to provide a clearance which captures and closely approximates a common thickness dimension. One convenient way to provide this clearance is to provide a base portion which is adapted to support the inside of the major arch of an arcuate orthopedic implant such as a femoral component, to provide a second structural member which has a portion that has a contour similar to at least a portion of the exterior major arch of the implant and to provide additional structure which holds the base portion a fixed distance from the second structural member which carries the contour. In a preferred embodiment the base portion has a quadrilateral bottom periphery and one or more vertical projections with the tallest vertical project being tall enough to support the largest of the implant (e.g. femoral) components in a series for which the package is designed. In other words, the top of this tallest vertical projection contacts the inside of the major arch of this largest component in such a way that the extreme edges of this major arch are suspended above the horizontal plane which includes the quadrilateral bottom periphery of the base portion. In a particularly preferred embodiment, the bottom of periphery of the base portion is generally rectangular in shape and the top of the tallest vertical projection is generally rectangular in shape. In an especially preferred embodiment the base portion has a series of vertical projections with their long edges parallel with the long edges of the bottom periphery of the base portion and configured as steps between the bottom periphery and the top of the tallest vertical projection. In one preferred embodiment one edge of the top surface of the tallest vertical projection is connected to an edge of the bottom periphery of the base portion by a wall which slants outwardly away from the center of the base portion.

One approach to holding the base portion and the second structural member in a fixed spacial relationship when retaining a arcuate implant component is to have both of them part of a unitary structure. In a preferred embodiment, the base portion is hingedly connected to two side portions via two opposing sides of its bottom periphery such that these side portions can be rotated toward each other. It is convenient to have at least a portion of the surface of one or both of these side portions which face the base portion have a contour similar to a portion of the exterior major arch of the largest component of the series the package is to accommodate. It is preferred that a portion of the top surface of the tallest vertical projection of the base and a portion of the facing surface of one of the side portions define the clearance that captures the approximate common thickness dimension of the series of implant components the package is to accommodate. In a particularly preferred embodiment, each side portion has a quadrilateral, more preferably a rectangular, base with a generally vertical wall rising from each of the three sides not hinged to the base portion. Each of these generally vertical walls has the same height as the other two and terminates in a horizontal ledge which extends inwardly. From each of these horizontal ledges an interior wall extends downwardly to the base of the side portion. In an especially preferred embodiment the interior wall which extends from the middle horizontal ledge has an arcuate shape. It is convenient if at least a portion of the arcuate wall of one of the side portions has a contour similar to at least a portion of the exterior major arch of the largest implant component in the series for which the package is designed.

One preferred embodiment of this unitary structure is a clamshell trifold in which a central portion has a generally rectangular base with a hinged connection along each of its long edges to a side portion with the external shape of a rectangular prism which lacks a wall arising from its hinged connection with the central portion, a bottom surface and most of its top surface. Each side portion does have a peripheral top surface which extends inward from its three side walls and terminates in a set of downwardly directed walls which define the interior of the side portion. The downwardly directed walls attached via the top surface to the short edges are generally vertical while the downwardly directed wall attached via the top surface to the long edge distal from the hinged connection has an arcuate shape. The partial top surfaces of the side portions are adapted to meet each other when the side portions are rotated about their hinged connections to the central portion and preferably these surfaces carry engaging means such as detents and mating projections so that the two top surfaces can be removably affixed to each other. The central portion is the base portion with the at least one vertical projection with a general rectangular top surface adapted to support the inner surface of the major arch of the implant components for which the package is designed.

Another approach to holding the base portion and the second structural member in a fixed spacial relationship when retaining an implant (e.g. femoral) component is to have both of them affixed to an inner tray of the type traditionally used in the packaging of medical implants which is modified in accordance with the present invention. The inventive tray has a quadrilateral bottom surface with a generally vertical side wall arising from each of its four peripheral edges to define a cavity adapted to contain the base portion, an implant component and the second structural member. This tray may have a horizontal ledge surrounding the periphery of its open mouth. In a preferred embodiment, the tray has a generally rectangular bottom surface. The bottom surface carries means for removable attachment to the base portion. One convenient approach is to have this bottom surface carry an upward projection with a periphery which is similar to the periphery of the interior periphery of the bottom of the base portion. The top surface of the tallest vertical projection of the base portion may conveniently carry a central projection adapted e.g. to lie between and closely adjacent to the condyles of the femoral components for which the package is designed. The second structural member may conveniently have a generally quadrilateral, preferably rectangular, peripheral shape which carries one or more arcuate surfaces which have contours which approximate the outer major arch of the implantl components for which the package is designed. In a preferred embodiment, the second structural member also carries a downward projection which may be adapted to fit the particular implant for which the package is designed, e.g. adapted to fit between the condyles of the femoral components. Means are provided for affixing the second structural member to the tray at a fixed distance from the base portion. One convenient means is a peripheral horizontal ledge on the second structural member which mates with the peripheral horizontal ledge of the tray. To provide for this mating without interfering with the ability to seal a film across the mouth of the tray, it is convenient for this horizontal ledge to have a depressed inner periphery with which to mate with the horizontal ledge on the second structural member. A portion of one or more of the arcurate surfaces of the second structural member and a portion or all of the top surface of the tallest vertical projection of the base portion establishes the clearance adapted to the approximate common thickness of the series of implant components for which the package is designed.

It is convenient to provide the package with venting means such that every surface of the package, as well as any arcuate orthopedic component that it may enclose, can be exposed to the sterilizing gases used in the preparation of sterile packaging of medical implants, although irradiation may be used in addition to, or instead of, gas sterilization. In the case of the clamshell approach, the trifold may be designed so that the three portions mate imperfectly leaving a gap so that these gasses can penetrate the interior, or vents can be specifically provided, or both approaches can be used together. In the case of the tray approach, the second structural member may be provided with a vent passage such as a gap in its surface and the base portion may be affixed to the bottom of the tray in such a way that the gasses can pass into the bottom of the base portion such as providing detents which cross the perimeter of the projection over which the base portion fits.

BRIEF DESCRIPTION OF THE DRAWINGS

FIG. 1 is a perspective view of the unitary package 10 showing the base portion 20 connected to the side portion 30 by rotatable hinges 40. The base portion 20 has a base periphery 21, a tallest vertical projection 22, recesses 23 adapted to accommodate the posts of those femoral components whose inner surface carries such posts, vertical projections 24 configured as steps, a slanting wall 26 which extends from the top wall of the tallest vertical projection 22 to the base periphery 21 and vents 27 which facilitate the access of sterilizing gasses to the interior of the packaging. The side portions 30 each have an arcurate wall 32, a horizontal ledge 36 and mating portions 38 of a reversible closing means. In addition, one of the side portions 30 has a central projection 34 adapted to fit between the condyles of the femoral components for which the packaging is designed.

DETAILED DESCRIPTION OF THE INVENTION

The present invention involves the design of packaging for arcuate orthopedic implants such as a series of spinal vertebrae components, cranium patches, limb sockets such as shoulder and hip sockets, and femoral components of various sizes for artificial knee joints, which have an approximate common thickness dimension. The common thickness dimension does not require that all the components in the series have an identical thickness dimension but just that this dimension does not so greatly vary over the size range as to make a common package impractical. The invention also involves the concept of designing such a common package with a clearance which captures this common dimension but also accommodates a range of sizes in the other dimensions of the implant components.

It is advantageous to construct the packaging such that the surfaces which contact the inner surfaces of the implant component have a high abrasion resistance. In this regard, implants such as femoral components are typically constructed with a generally convex configuration with the inner surfaces of the major arc having a fairly rough surface to promote adhesion to the bones which will carry them when they are implanted. One type of surface with advantageous abrasion resistance is based upon thermoplastic aromatic polyether polyurethane. Deerfield Urethanes, a subsidiary of Bayer, markets suitable thermoplastic aromatic polyether polyurethane films under the trademark Dureflex® with grade PT9400 being particularly suitable. It is also advantageous to use this polyurethane surface to protect to the exterior polished treated surface typical of many implant components such as femoral components.

It is also advantageous to construct the packaging out of materials which can be readily thermoformed into packages of suitable rigidity to support the largest component of the series for which the packaging is designed. The typical packaging material for medical implants including femoral components has been films of polyethylene terephthalate glycol (PETG) because they have adequate rigidity and mechanical strength and good thermal formability. However, it is desirable to have greater abrasion resistance than this material offers. It is convenient to laminate these films to films of thermoplastic aromatic polyether polyurethane and configure the packaging such that it is the polyurethane surface which faces the rough surfaces of the femoral component. The laminate is conveniently formed by melt laminating the polyurethane to the PETG. A preferred PETG for this lamination is Eastman's Eastar 6763 PETG resin. The thicknesses for both films should be compatible with both thermoforming the package configuration and providing adequate mechanical strength. A convenient range for the polyurethane is between about 0.01 and 0.025 inches while for the PETG it is between about 0.015 and 0.04 inches.

The packages with which the present invention is concerned can be conveniently designed using computer-aided design (CAD). One approach is to create three dimensional depictions of all the implant components in a given series such as the size range offered by a given manufacturer and then overlay them to determine the location and size of a common dimension. Commonly, this is the thickness at the top of the major arch. Then a package can be designed which provides a clearance which closely approximates this common dimension and also accommodates the largest size implant component in the series.

Figure 1:
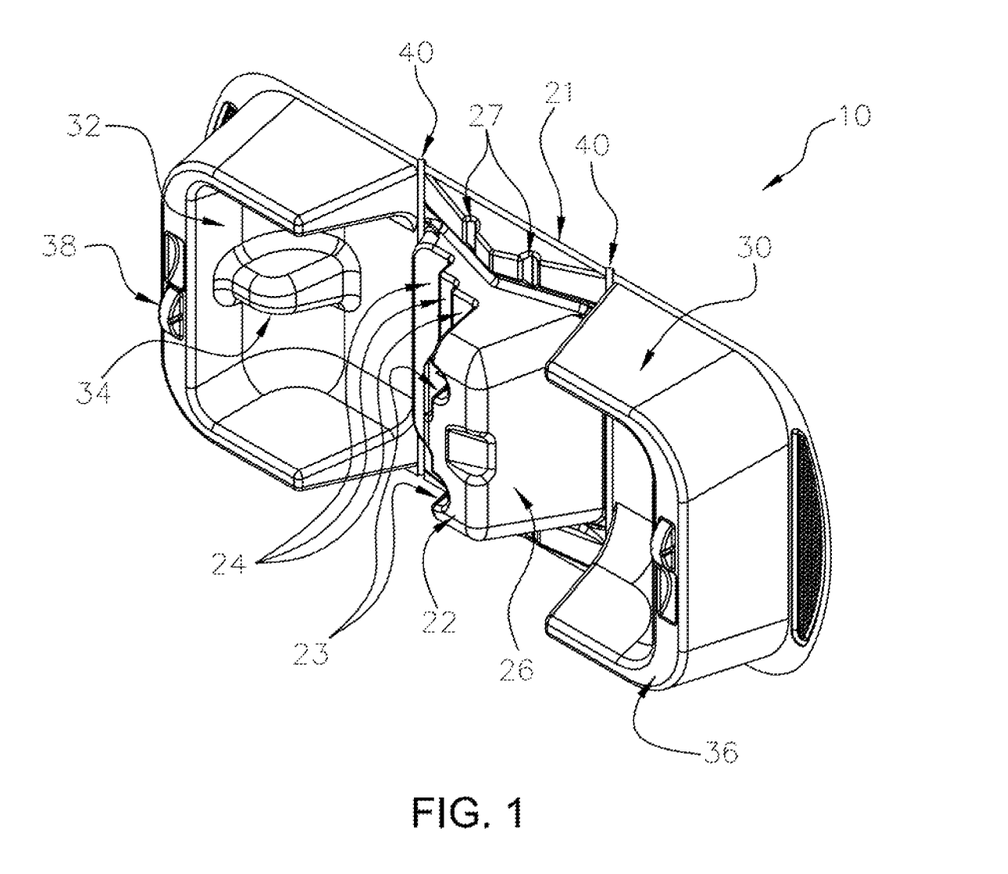
Figure 2:
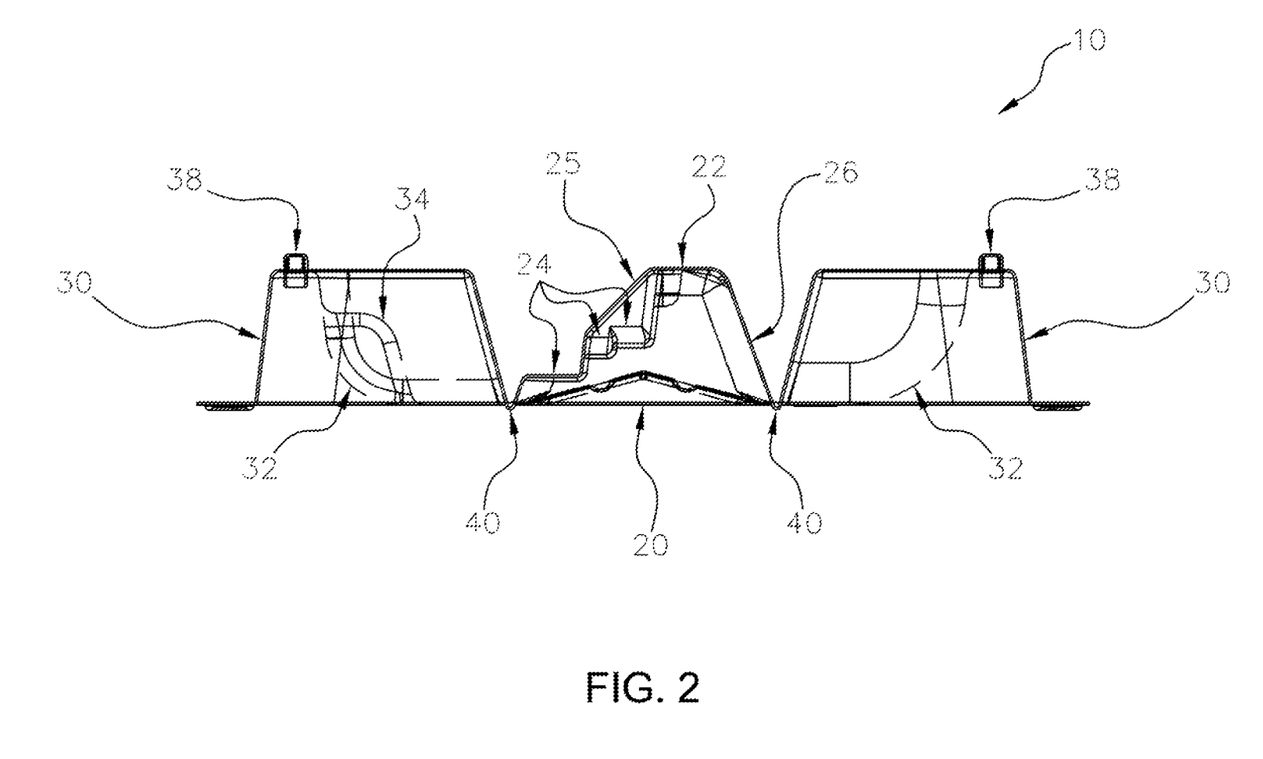
FIG. 2 is a side elevation view of the unitary package 10 showing the base portion 20 having a tallest vertical projection 22, carrying vertical projections 24 configured as steps and having a ramp 25 adapted to fit between the condyles of the femoral components for which the packaging is designed. The side portions 30 are shown having arcurate walls 32 and the mating portions 38 of a reversible closing means. In addition one of the side portions 30 has a central projection 34 adapted to fit an arcuate orthopedic implant for which the packaging is designed, e.g. between the condyles of the femoral components.

The clearance which is used to capture the common thickness dimension is preferably between about 0 and 0.125 inches, more preferably between about 0.010 and 0.050 inches. The minimum design clearance between a packaged component and the package preferably ranges between about 0 and 0.0325 inches. These are suitable dimensions e.g. for femoral components One approach to the packaging of a series of implants is illustrated in FIG. 1-2 by way of example with respect to femoral components. In this approach the base portion 20 is configured as part of a unitary structure 10 with rotatable side portions 30 which function as a second structural member to establish the clearance which approximates the approximate common thickness dimension of the series of femoral components for which the packaging is designed. The two side portions 30 can be rotated about the hinges 40 to meet each other and completely enclose the base portion 20. The arcuate walls 32 of the side portions 30 cooperate with the top of the tallest vertical projection 22 to establish this clearance when rotated to meet each other. In this regard, the hinges 40 need simply be the grooves well known in the art of thermoformed parts for allowing rotation between adjacent elements of a part. The top of the tallest vertical projection 22 is adapted to support a portion of the inner surface of the major arch of the femoral components. The base portion carries two recesses 23 to accommodate the posts which the inner surface of some femoral components carries. The extreme ends of the condyles of the femoral components may be supported one of the vertical projections 24, depending upon the size of a given component. The ramp 25 is adapted to fit between the condyles of the femoral components and may contact the condyles depending upon the size of a given component. The slanting wall 26 serves to accommodate the end of the major arch of the femoral components which is distal from the condyles and with the arcuate wall 32 which it faces, when the side portions are rotated to meet each other, it serves to narrowly constrict this end of the component. The horizontal ledges 36 are adapted to meet each other thus limiting the rotation of the two side portions toward each other. Each horizontal ledge 36 carries a mating portion 38 of a reversible closing means. When the side portions 30 are rotated towards each other so that the ledges 36 meet, these mating portions 38 interlock to hold the unitary package 10 in a closed configuration but interlock in a manner that a person of average strength can readily disengage them when it is desired to open the package. One arcuate wall 32 carries a central projection 34 which is adapted to fit between the condyles of the femoral components and may contact the condyles depending upon the size of a given component. It cooperates with the ramp 25 to limit the range of motion of the femoral components. Finally the base portion is equipped with vents 27 which facilitate the access of sterilizing gas to the interior of the packaging when it is in a closed configuration.

The unitary package 10 is adapted to be placed into an inner tray of the type common in medical implant packaging. Because it carries no contaminates such as residual adhesive from the lid stock and can be readily sterilized and kept sterile in an appropriate inner tray, it can be placed on the surgical tray for ready access by the clean surgical team. Thus it can serve to protect the femoral component which it contains from damage or any bodily fluid or tissue spatter during an operation until the component is accessed for insertion. The unitary package 10 also provides a convenient presentation of the femoral component to the clean surgical team.

Figure 3:
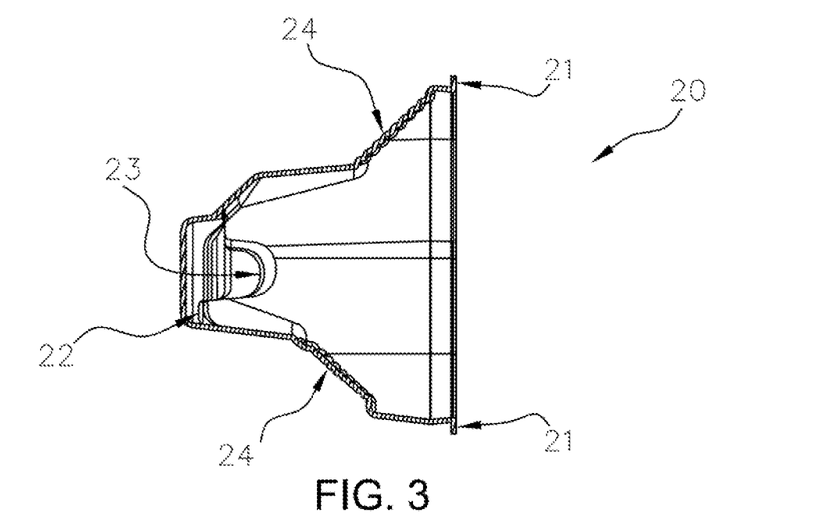
FIG. 3 is a cross section of the base portion 20 along line 3-3 of FIG. 4, showing its base periphery 21, its tallest vertical projection 22, its post recesses 23 and its vertical projections configured as steps 24.
Figure 3A:
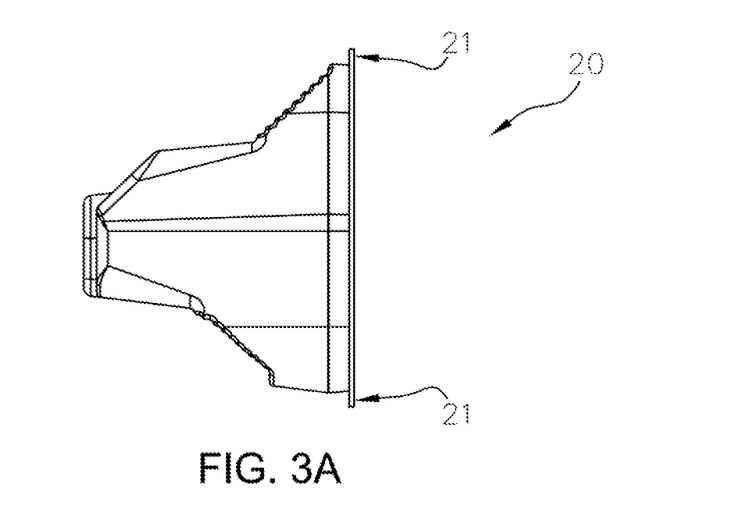
FIG. 3A is a side elevation of the base portion 20 showing its base periphery 21.
Figure 4:
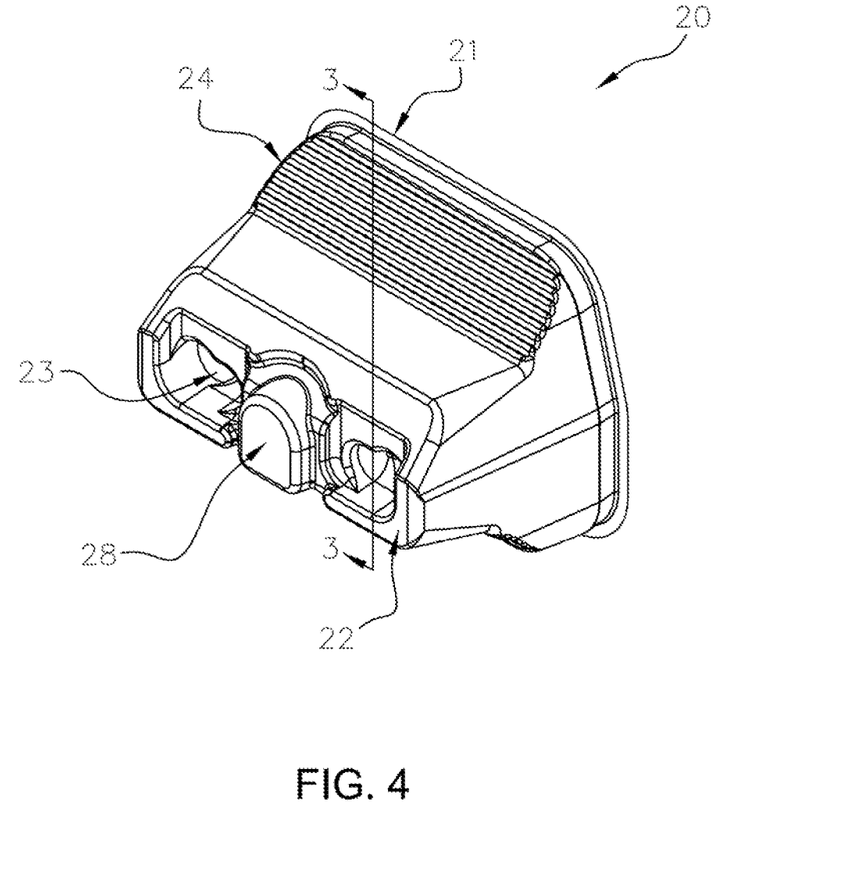
FIG. 4 is a prospective view of the base portion 20, additionally showing its top wall projection 28 to accommodate e.g. the condyles of the femoral component to be packaged.
Figure 5:
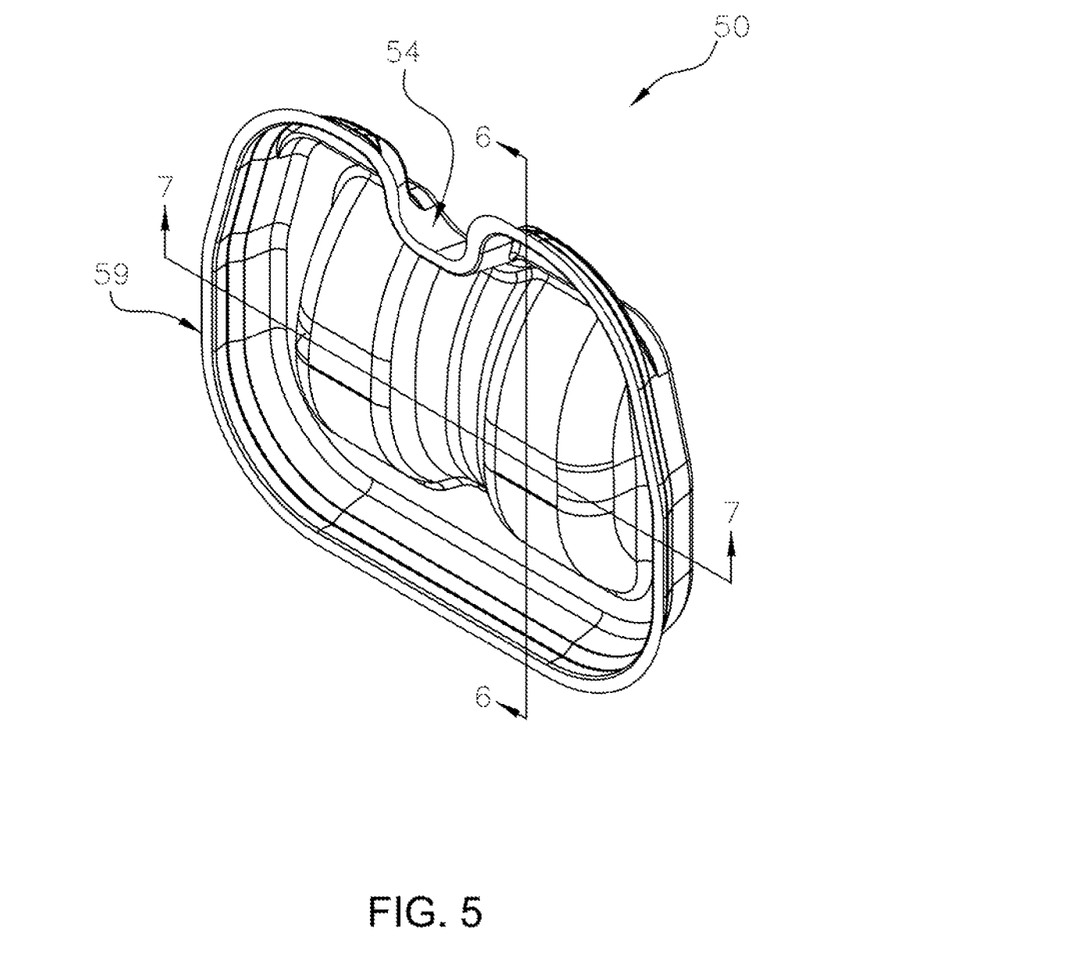
FIG. 5 is a prospective view of the retainer portion 50 (representative second structural member), showing its vent opening 54 and its supporting ledge 59.
Figure 6:
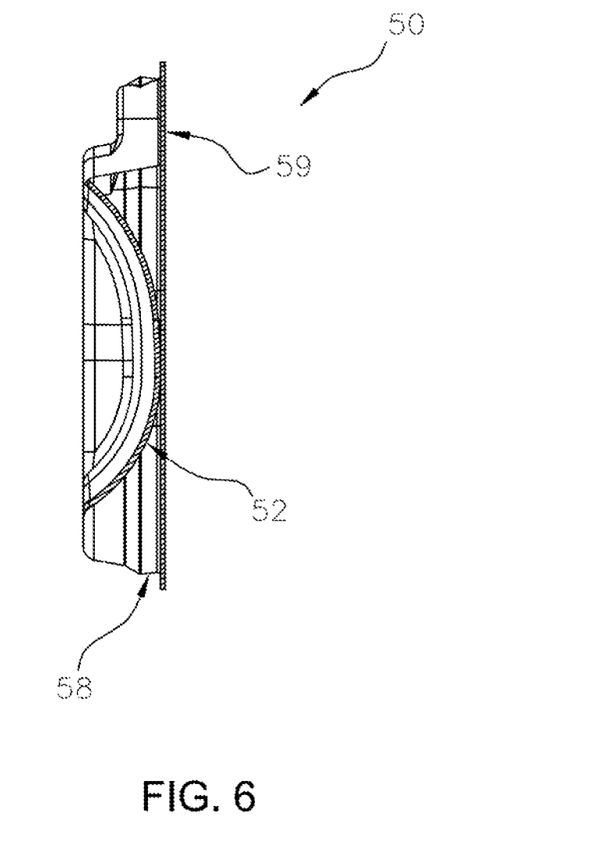
FIG. 6 is a cross-sectional view of the retainer portion 50 taken along line 6-6 of FIG. 5 showing its arcurate wall 52, its peripheral locking surface 58 and its supporting ledge 59.
Figure 7:
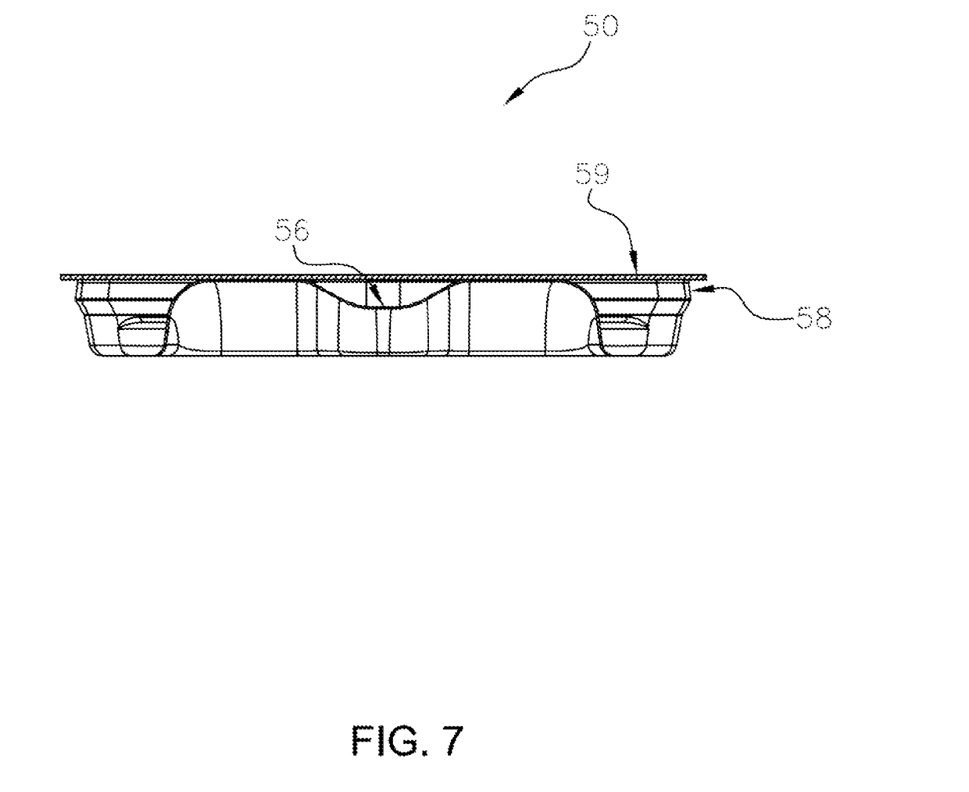
FIG. 7 is a cross-sectional view of the retainer portion 50 taken along line 7-7 of FIG. 5 showing its condyle engaging central groove 56, its peripheral locking surface 58 and its supporting ledge 59.
Figure 8:
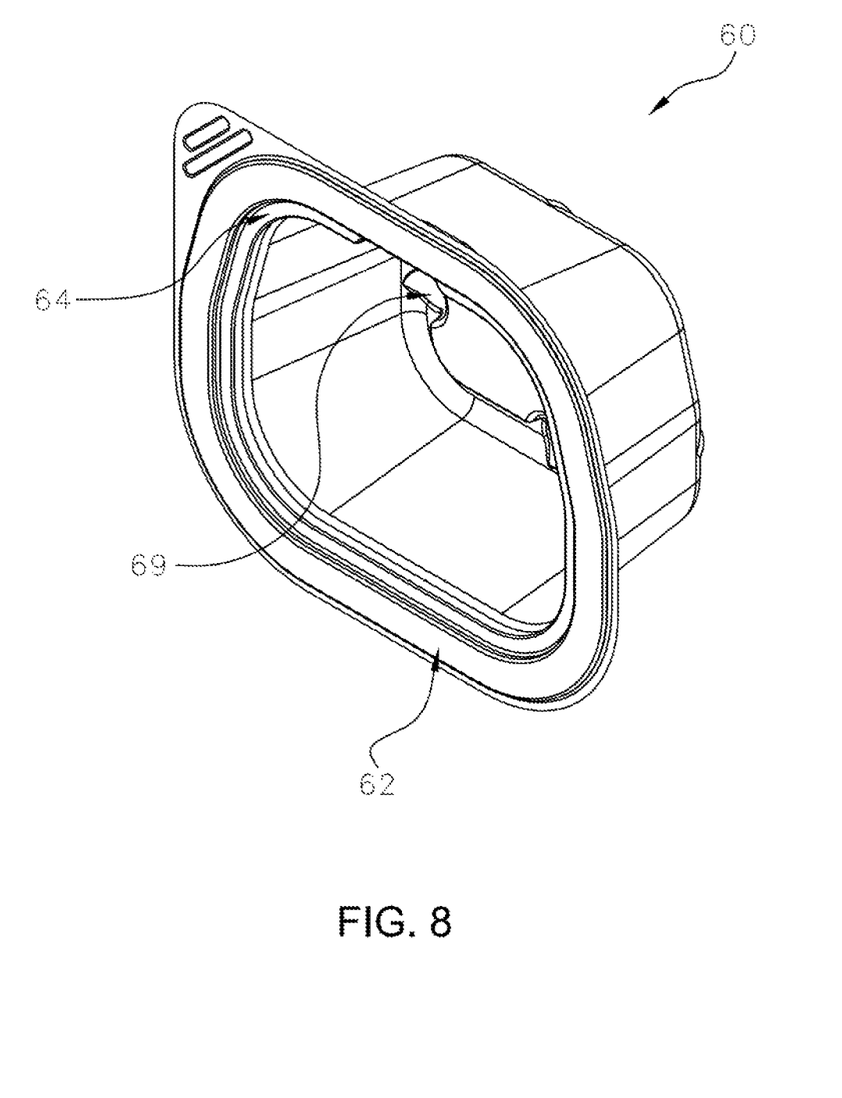
FIG. 8 is a perspective view of the inner tray 60 showing its sealing surface 62, its supporting ledge 64 and its vents 69.
Figure 9:
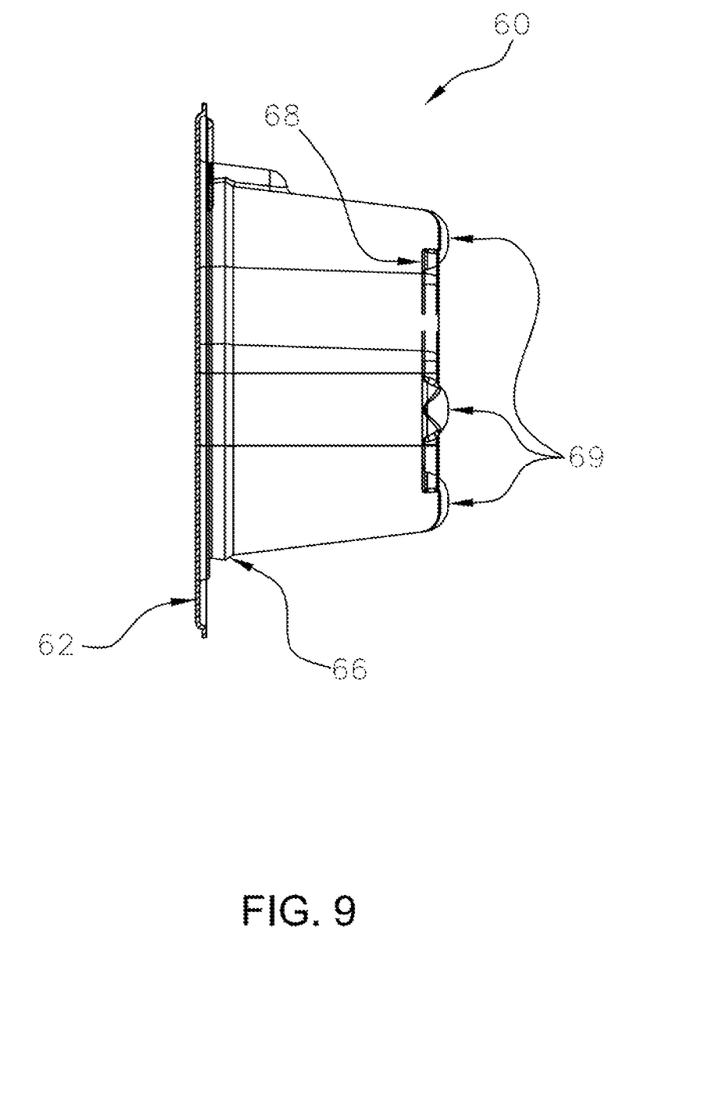
FIG. 9 is a side elevation of the inner tray 60 showing its sealing surface 62, its peripheral locking surface 66, its upward projection 68 and its vents 69.

Another approach to the packaging of a series of arcuate orthopedic implants such as femoral components is illustrated in FIG. 3-9. In this approach the base portion 20 is configured as an insert as illustrated in FIGS. 3, 3A and 4. It cooperates with a second structural member configured as a retainer 50, as illustrated in FIG. 5-7, and a specially adapted inner tray 60, which is illustrated in FIG. 8-9. The base portion 20 has a bottom periphery 21 which force fits over the upward projection 68 of the inner tray 60 to lock the two pieces together. It also has a tallest vertical projection 22 which is adapted to accommodate a portion of the inner surface of the major arc of the implant components and mainly support their weight. In addition, it has recesses 23 which accommodate the posts which extend from the inner surface of some femoral components. It further has vertical projections 24 which are configured as steps to accommodate the extreme ends of the major arch of some femoral components. Finally, it has a top wall projection 28 which is adapted to accommodate e.g. the condyles of the femoral components by fitting between them.

The retainer 50 cooperates with the base portion 20 to create a clearance for capturing the common thickness dimension of the series of implant components for which the package is adapted. In particular, the arcurate walls 52 of the retainer 50 are held a constant distance from the tallest vertical projection 22 of the base portion 20 to establish this clearance. These arcurate walls 52 have a contour which approximates that of a portion of the outside surface of the major arch of the implant components belong to this series. The retainer 50 also has a vent 54 which facilitates the circulation of sterilizing gasses about the contents of the inner tray 60 and also serves as a finger grip with which to remove the retainer 50 from the inner tray 60. In addition, it has a central groove 56 which is adapted to engage the components, e.g. condyles of the femoral components, by fitting between them. It also a peripheral locking surface 58 which cooperates with the peripheral locking surface 66 of the inner tray 60 to hold the retainer 50 in place. Finally it has a supporting ledge 59 which cooperates with the supporting ledge 64 of the inner tray 60 to support its weight.

The inner tray 60 holds the base portion 20 and the retainer 50 in a fixed spacial relationship to create a package interior which accommodates a series of implant components of different sizes and provides a clearance which approximates the approximate common thickness dimension of this series. It also has the traditional sealing surface 62 which accommodates the adhesive sealing of a film across the open mouth of the inner tray 60. It additionally has vents 69 which provide access to the interior of the base portion 20 for the sterilizing gasses.

Figure 10:
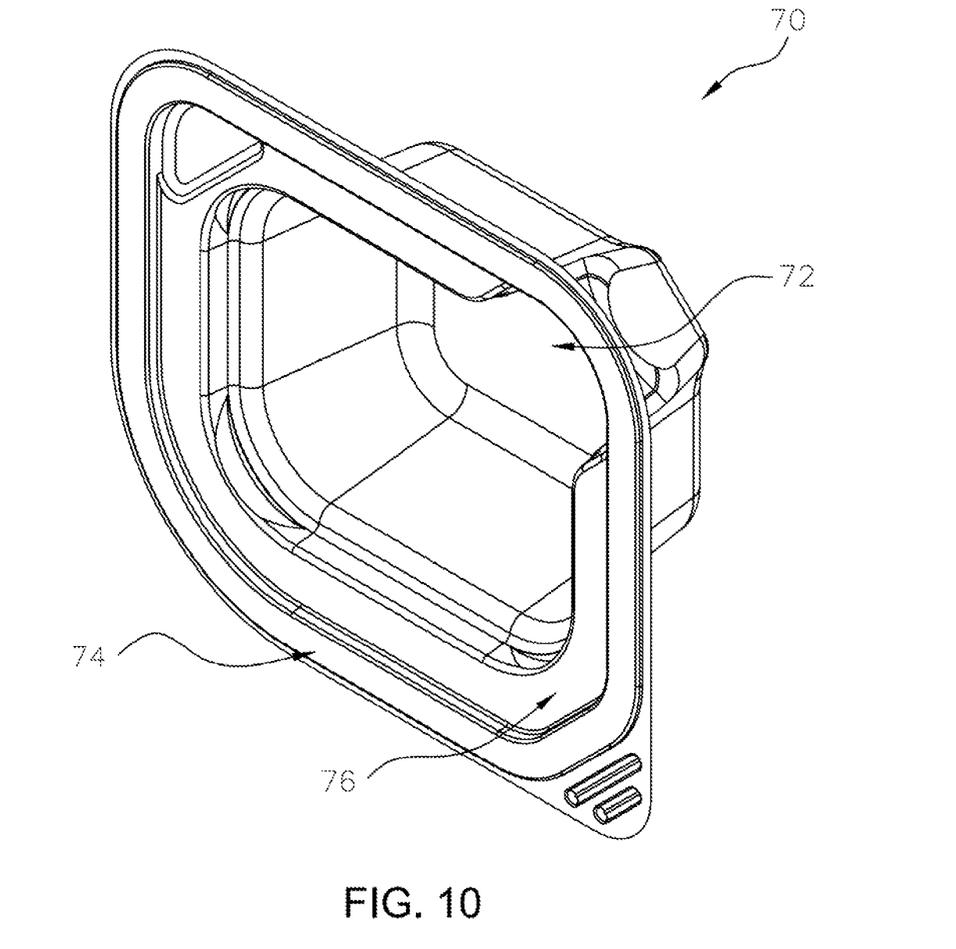
FIG. 10 is a perspective view of the outer tray 70 into which the inner tray 60 is placed to establish a double seal sterile system showing its vent 72 for sterilizing gasses, its sealing surface 74 for the adhesive adherence of closure film and its supporting ledge 76 which supports the inner tray 60.

In both approaches it is contemplated that the inner tray will in turn be placed in an outer tray 70 as illustrated in FIG. 10. This creates a double protection system such that the sterile integrity of the inner tray is protected from comprise by handling damage by the outer tray. This outer tray 70 has a vent 72 to facilitate the access of sterilizing gasses when an inner tray has been inserted and the lid stock has been applied. The outer tray has a sealing surface 74 for the adhesive application of lid stock and a supporting ledge 76 to support the inner tray.

WORKING EXAMPLES

Example I

A unitary package 10 was constructed of a melt lamination of 0.01 inch thick Duraflex®PT 9400 aromatic polyether polyurethane onto 0.02 inch thick Eastar® 6763 PETG by thermoforming. The overall package had a length of 10" when open with each side portion 30 having a length of 2.571" and the base portion 20 having a length of about 4.86". The side portions 30 each had a height of 1.750" and the tallest vertical projection 22 of the base portion 20 had a height of 1.750" as well. There were three vertical projections 24 with heights of 0.364", 0.680" and 0.800". The post recesses were about 0.468" in depth. The package had an overall width of approximately 5". The top wall of the tallest vertical projection 22 had a width of about 2.963" The hinges 40 were grooves about 0.125" wide.

This unitary package could accommodate a range of sizes of femoral components such that each was held in the closed package rather tightly with minimal readily noticeable movement within the package on shaking.

Example 2

A base portion 20 configured as an insert and a retainer 50 were each constructed of a melt lamination of 0.01 inch thick Duraflex®PT 9400 aromatic polyether polyurethane onto 0.025 inch thick Eastar® 6763 PETG by thermoforming. The base periphery 21 of the base portion was an approximate rectangle 3.5" by 2.59". Its tallest vertical projection 22 had a height of about 1.875". The top wall projection 28 was approximately a rectangle 0.624" by 0.661" and had a height of about 0.095". It had a series of vertical projections 24 of lesser height on either side of the tallest vertical projection 22. The recesses 23 for the posts were about 0.42" in diameter and about 0.542" deep measured from the top of the tallest vertical projection 22. The retainer 50 had a roughly rectangular shape of 4.733" by 3.826". It had arcurate walls 52 of about 2.96" in the plane of the retainer 50 parallel to the shorter side. These arcurate walls 52 rose above the plane of the retainer 50 to a maximum height of 0.564". The distance from the plane of the retainer 50 to its supporting ledge 59 was about 0.564".

An inner tray 60 was constructed of 0.04 inch thick Eastar® 6763 PETG by thermoforming. It had a height of about 2.318" with a step down to its supporting ledge 59 of about 0.125". Its cavity viewed from the top was approximately a rectangle 4.551" by 3.640". When the base portion 20 and the retainer 50 were affixed to it, it held them in a fixed special relationship to each other.

This three piece structure was used to package a series of implant (femoral) components of different sizes and each size component was rather tightly held with minimal readily noticeable movement within the package on shaking. The closest clearance of the assembled package was a gap of about 0.3256" between the top of the tallest vertical projection 22 of the base portion 20 and the arcurate walls 52 of the retainer 50. For the largest of the femoral components in the series this left a clearance of about 0.009" when this component was placed in the package and for the smallest of the femoral components in the series this left a clearance of about 0.0102". The femoral components in this series ranged in size from about 1.902" to 2.8795", viewing the components oriented like a letter "C" and measuring between the highest and lowest points on the "C".

CAD modeling established that a single package was able to accommodate forty different femoral components comprising left and right hand versions of two styles and ten sizes within each style.

Embodiments of the Invention

1. A package adapted to securely hold for shipment any one of a series of implant components of different sizes comprising:
   a. a base portion which has a quadrilateral base and a vertical projection with a top surface adapted to support a portion of the inner surface of the major arch of the implant components of said series,
   b. a second structural member which has an arcuate surface whose contour approximates a portion of the outside surface of the major arch of the implant components in said series; and
   c. means for holding said second structural member in a fixed spacial relationship with said base portion so as to define a clearance which approximates an approximate common thickness dimension shared by the members of said series.

2. The package according to embodiment 1 wherein said base portion and said second structural member are fabricated of a laminated thermoplastic such that the surfaces which are adapted to face the implant components to be packaged are an aromatic polyether polyurethane.

3. The package according to embodiment 1 or 2 wherein said implant components are femoral components of prosthetic knee joints.

4. An easily openable presentation package for any one of a series of implant components of different sizes comprising:
   a. a base portion with a generally quadrilateral peripheral shape with at least one vertical projection;
   b. two generally quadrilateral side portions, each hingedly attached to one of two opposed edges of the periphery of said base such that an edge of each side portion is essentially coextensive with one of said opposed edges of the periphery of said base, each of said side portions having
      i. a set of three outer vertical walls rising from the three peripheral edges not hingedly connected to said base;
      ii. a generally horizontal ledge extending inward from each of said vertical walls;
      iii. a arcuate wall extending downward from the middle ledge to intersect with a horizontal plane which encompasses said peripheral edges of said base portion and a generally vertical wall extending downward from each of the other two generally horizontal ledges to also intersect with said horizontal plane;
      iv. wherein one of said vertical projections from said base and said arcuate wall extending from said middle ledge of one of said side portions are configured such that when said portion is rotated about its hinged connection with said base portion to bring its ledges into a generally vertical configuration or to meet with the ledges of said other side portion, said vertical projection and said arcuate wall define a clearance which approximates an approximate common thickness dimension of a series of implant components which are each of a different size.

5. The package according to embodiment 4 wherein said implant components are femoral components of prosthetic knee joints.

6. The presentation package according to any one of embodiments 4 or 5 wherein:
   a. said base portion has:
      i. a generally rectangular base peripheral shape;
      ii. a series of vertical projections of varied heights with at least the tallest projection having its base coextensive with the a portion of a long edge of said base peripheral shape and having a generally rectangular top surface;
   b. said clearance approximating said approximate common dimension is defined by the distance between a portion of said tallest vertical projection and one of said arcurate walls when the side portion which carries said arcurate wall is rotated about its hinged connection with said base portion to bring its ledges into a generally vertical configuration or to meet with the ledges of said other side portion.

7. The presentation package according to embodiment 6 wherein said series of vertical projections are configured as steps from the periphery of said base to said tallest vertical projection.

8. The presentation package according to any one of embodiments 6-7 wherein the wall connecting said top surface of said tallest vertical projection to the portion of its base partially coextensive with one of the long edges of peripheral shape said base slants outwardly away from the center of said base portion.

9. The presentation package according to any one of embodiments 6-8 wherein said arcurate walls of said side portions have each have a contour that approximates a portion of the outside contour of the largest of said series of implant components of different sizes with an approximate common dimension.

10. The presentation package according to any one of embodiments 8-9 wherein said slanted wall and the arcurate wall it faces when the side portion which carries said arcurate wall is rotated about its hinged connection with said base portion to bring its ledges into a generally vertical configuration or to meet with the ledges of said other side portion define a clearance which closely envelopes the rear portion of said series of implant components which have an approximate common thickness dimension but are each otherwise of a different size.

11. The presentation package according to embodiment 10 wherein said implant components are femoral components of prosthetic knee joints, and wherein the arcurate wall not facing said slanted wall has projection approximately in its center which, when the side portion which carries said arcurate wall is rotated about its hinged connection with said base portion to bring its ledges into a generally vertical configuration or to meet with the ledges of said other side portion, faces inward towards said vertical projections of said base and is adapted to fit between the condyles of said series of femoral components.

12. The presentation package according to any one of embodiments 6-11 wherein said other two generally vertical walls of each side portion deviate a minor amount from strictly vertical to slope inwardly toward the cavity which they and said arcurate wall define.

13. The presentation package according to any one of embodiments 4-12 which is fabricated from a laminated thermoplastic such that the surfaces which are adapted to face the implant components to be packaged are an aromatic polyether polyurethane.

14. A package for the transport and handling of any one of a series of implant components of different sizes comprising:
   a. an insert portion having
      i. a generally rectangularly shaped horizontal base;

ii. a generally rectangularly shaped top which is narrower than, generally parallel to and spaced from said base;
iii. two side walls connecting the shorter sides of said base to said top, said walls being generally vertical so as to connect the portions of the top which lie generally above the shorter edges of said base to said shorter edges; and
iv. two long walls connecting the long edges of said base to the long edges of said top with one or both of said long walls having a portion at an angle between vertical and horizontal which accommodates the fact that said top is narrower than said base, said angled portion or portions optionally carrying a series of steps;
b. a retainer portion with a surface which generally follows the outside contours of the central portion of an implant component and being so dimensioned that it defines a narrow range of clearances between a portion of said top of said insert and a portion of its contoured surface when held a fixed distance from said top; and
c. a tray comprising a bottom wall and four sidewalls which define a volume into which said insert and said retainer fit, said tray having engaging means for holding said insert and said retainer in said volume and keeping them at fixed distance from each other such that said narrow range of clearances approximates an approximately common dimension of a series of implant components which are each otherwise of a different size.

15. The package according to embodiment 14, wherein said implant components are femoral components of prosthetic knee joints.

16. The package according to any one of embodiments 14-15 wherein said generally rectangularly shaped top of said insert portion is provided with a generally rectangularly shaped vertical projection which has its long sides parallel to the short sides of said top, said vertical projection being located in the center of said top.

17. The package according to any one of embodiment 14-16 wherein said generally rectangularly shaped top is provided with two generally circularly shaped recesses spaced evenly from the center of said top along its longer dimension.

18. The package according to any one of embodiment 14-17 wherein the bottom wall of said tray has a vertical projection which is offset inwardly from but follows the periphery of said bottom wall and the inner periphery of the bottom of said insert force fits over said projection to hold said insert in place in the cavity of said tray.

19. The package according to embodiment 18 wherein said bottom wall and said vertical projection carry vents which allow gaseous access to the interior surfaces of said insert when it is affixed to said tray via said vertical projection.

20. The package according to any one of embodiment 14-19 wherein said tray has a horizontal ledge about the mouth of its cavity which is surrounded by a higher horizontal ledge, said lower ledge being adapted to support said retainer portion.

21. The package according to embodiment 20 wherein a vertical wall depends from the inner edge of said lower ledge and is offset outwardly from said four sidewalls of said tray and said retainer portion has a vertical wall offset inwardly from its outer periphery, said retainer portion vertical wall force fitting within said inner tray vertical wall to hold said retainer portion in place on said tray.

22. The package according to any one of embodiment 14-21 wherein said retainer portion is generally rectangularly shaped, has a groove in its center running in its shorter direction and has two arcurate walls of equal dimensions, one on each side of said groove, which run in the same direction as said groove and extend a greater height out of the plane of said retainer portion than said groove.

23. The package according to embodiment 22 wherein said insert portion and said retainer portion are both fabricated of a laminated thermoplastic such that the surfaces which are adapted to face the implant components to be packaged are an aromatic polyether polyurethane.

24. The package according to any one of embodiments 14-22 wherein said insert portion and said retainer portion are unitary being formed of a single piece having a hinged connecting wall portion.

The above disclosure is for the purpose of illustrating the present invention and should not be interpreted as limiting the present invention to the particular embodiments described but rather the scope of the present invention should only be limited by the claims which follow and should include those modifications of what is described which would be readily apparent to one skilled in the art.

What is claimed is:

1. A package adapted to securely hold for shipment any one of a series of implant components of different sizes comprising:
a. a base portion having a quadrilateral base and a vertical projection with a top surface adapted to support a portion of an inner surface of a major arch of the implant components of said series; and
b. a structural member having an arcuate surface with a contour that approximates a portion of an outside surface of the major arch of the implant components in said series;
c. wherein said structural member includes one or more mating portions for holding said second structural member in a fixed spatial relationship with said base portion so as to define a clearance of up to about 0.125 inches between the vertical projection of said base portion and the arcuate surface of said structural member to approximate an approximate common thickness dimension shared by the implant components of said series.

2. The package of claim 1 wherein said base portion and said structural member are fabricated of a laminated thermoplastic such that one or more surfaces of said base portion and said structural member which are adapted to face the implant component to be packaged are an aromatic polyether polyurethane.

3. The package of claim 1 wherein said implant components are femoral components of prosthetic knee joints.

4. An easily openable presentation package for any one of a series of implant components of different sizes comprising:
a. a base portion including a generally quadrilateral peripheral shape and at least one vertical projection;
b. two generally quadrilateral side portions, each hingedly attached to one of two opposed edges of a periphery of said base portion such that an edge of each side portion is essentially coextensive with one of said opposed edges of the periphery of said base portion, each of said side portions having;
i. a set of three outer vertical walls extending from respective peripheral edges of said side portion not hingedly attached to said base portion;
ii. a generally horizontal ledge extending inward from each of said vertical walls;

iii. an arcuate wall extending downward from a middle ledge to intersect with a horizontal plane which encompasses said peripheral edges of said base portion and a generally vertical wall extending downward from each of the two generally horizontal ledges to also intersect with said horizontal plane;

iv. wherein one of said vertical projections from said base portion and said arcuate wall extending from said middle ledge of one of said side portions is configured such that when one of said side portions is rotated about said hinged attachment with said base portion to bring said generally horizontal ledge of said side portion into a generally vertical configuration or to meet with said generally horizontal ledge of said other side portion, said vertical projection and said arcuate wall define a clearance of up to about 0.125 inches to approximate an approximate common thickness dimension of a series of implant components which are each of a different size.

5. The package of claim 4 Wherein said implant components are femoral components of prosthetic knee joints.

6. The presentation package of claim 4 wherein:
   a. said base portion has:
      i. a generally rectangular base peripheral shape; and
      ii. a series of vertical projections of varied heights, wherein at least a tallest vertical projection of the series of vertical projections includes a base coextensive with a portion of an edge of said base peripheral shape and has a generally rectangular top surface;
   b. wherein said clearance is defined by a distance between a portion of said tallest vertical projection and one of said arcuate walls when said side portion which carries said arcuate wall is rotated about said hinged attachment with said base portion to bring said generally horizontal ledge of said side portion into a generally vertical configuration or to meet with said generally horizontal ledge of said other side portion.

7. The presentation package of claim 6 wherein said series of vertical projections are configured as steps extending from a periphery of said base to said tallest vertical projection.

8. The presentation package of claim 6 wherein said tallest vertical projection includes a slanted wall connecting said top surface to said portion of said base peripheral shape, wherein said slanted wall slants outwardly away from a center of said base portion.

9. The presentation package of claim 6 wherein said arcuate walls of said side portions each have a contour that approximates a portion of an outside contour of a femoral implant component.

10. The presentation package of claim 8 wherein said slanted wall and said arcuate wall facing said slanted wall when the side portion which carries said arcuate wall is rotated about said hinged attachment with said base portion to bring said generally horizontal ledge of said side portion into a generally vertical configuration or to meet with said generally horizontal ledge of said other side portion define a clearance configured to closely envelope a rear portion of said series of implant components which have an approximate common thickness dimension but are each otherwise of a different size.

11. The presentation package of claim 10 wherein said implant components are femoral components of prosthetic knee joints, and
   wherein the arcuate wall not facing said slanted wall has a projection located approximately at a center of the arcuate wall which, when the side portion which carries said arcuate wall is rotated about said hinged attachment with said base portion to bring said generally horizontal ledge of said side portion into a generally vertical configuration or to meet with said generally horizontal ledge of said other side portion, faces inward towards said vertical projections of said base and is adapted to fit between a plurality of condyles of said series of femoral components.

12. The presentation package of claim 6 wherein said other two generally vertical walls of each side portion slope inwardly toward a cavity defined by said other two generally vertical walls and said arcuate wall.

13. The presentation package of claim 4 which is fabricated from a laminated thermoplastic such that one or more surfaces which are adapted to face the implant components to be packaged are an aromatic polyether polyurethane.

14. A package for the transport and handling of any one of a series of implant components of different sizes comprising:
   a. an insert portion having;
      i. a generally rectangular shaped horizontal base;
      ii. a generally rectangular shaped top which is narrower than, generally parallel to, and spaced from said base;
      iii. a first pair of side walls connecting a first pair of sides of said base to a first pair of edges of said top, said first pair of side walls being generally vertical so as to connect said top to said base; and
      iv. a second pair of side walls connecting a second pair of sides of said base to a second pair of edges of said top, wherein one or both of said second pair of side walls includes a portion oriented at an angle between vertical and horizontal, and wherein said second pair of side walls are longer than said first pair of side walls;
   b. a retainer portion having a surface defining a clearance of up to about 0.125 inches between a portion of said top of said insert and a portion of said surface of said retainer when held a fixed distance from said top; and
   c. a tray comprising a bottom wall and four sidewalls defining an opening into which said insert and said retainer fit within, said tray having engaging means for holding said insert and said retainer in said volume at said fixed distance from each other such that said clearance approximates an approximately common dimension of a series of implant components which are each otherwise of a different size.

15. The package of claim 14, wherein said implant components are femoral components of prosthetic knee joints.

16. The package of claim 14 wherein said generally rectangular shaped top of said insert portion includes a generally rectangular shaped vertical projection located at a center of said top.

17. The package of claim 14 wherein said generally rectangular shaped top includes two generally circular shaped recesses spaced evenly from the center of said top.

18. The package of claim 14 wherein the bottom wall of said tray has a vertical projection which is offset inwardly from, but follows a periphery of, said bottom wall, and wherein an inner periphery of the bottom of said insert is configured to force fit over said vertical projection to hold said insert in place in the opening of said tray.

19. The package of claim 18 wherein said bottom wall and said vertical projection include one or more vents which allow gaseous access to the interior surfaces of said insert when said insert is affixed to said tray via said vertical projection.

20. The package of claim 14 wherein said tray has a first ledge at least partially surrounding said opening and a second ledge surrounding said first ledge, wherein said first ledge is disposed below said second ledge and is configured to support said retainer portion.

21. The package of claim 20 wherein said tray includes a vertical wall extending from an inner edge of said first ledge and is offset outwardly away from said four sidewalls of said tray, wherein said retainer portion has a vertical wall offset inwardly from an outer periphery of said retainer portion and configured to be force fit within said inner tray to hold said retainer portion in place relative to said tray.

22. The package of claim 14 wherein said retainer portion has a generally rectangular shape and comprises:
   a groove located at a center of said retainer portion, and
   two arcuate walls of equal dimensions located at opposites sides of said groove, respectively, and are oriented in the same direction as said groove and extend a height greater than a height of said groove.

23. The package of claim 22 wherein said insert portion and said retainer portion are both fabricated of a laminated thermoplastic such that one or more surfaces of said insert portion and said retainer portion which are adapted to face the implant components to be packaged are an aromatic polyether polyurethane.

24. The package of claim 14 wherein said insert portion and said retainer portion are a unitary structure including a hinged connecting wall portion connecting said insert portion with said retainer portion.

* * * * *

UNITED STATES PATENT AND TRADEMARK OFFICE
CERTIFICATE OF CORRECTION

PATENT NO.         : 9,433,469 B2
APPLICATION NO.    : 14/391133
DATED              : September 6, 2016
INVENTOR(S)        : Tad R. Kinyon Page 1 of 3

It is certified that error appears in the above-identified patent and that said Letters Patent is hereby corrected as shown below:

On the Title Page

Item (56), in Column 2, under "Foreign Patent Documents", Line 1, delete "2007076503", and insert -- 2007076603, --.

Item (57), in Column 2, under "Abstract", Line 13, delete "arcurate"," and insert -- arcuate, --.

In the Specification

In Column 2, Line 53, delete "arcurate" and insert -- arcuate --.

In Column 2, Line 54, delete "arcurate" and insert -- arcuate --.

In Column 3, Line 5, delete "arcurate" and insert -- arcuate --.

In Column 3, Line 40, delete "arcurate" and insert -- arcuate --.

In Column 3, Line 41, delete "implantl" and insert -- implant --.

In Column 3, Line 56, delete "arcurate" and insert -- arcuate --.

In Column 4, Line 25, delete "arcurate" and insert -- arcuate --.

In Column 4, Line 37, delete "arcurate" and insert -- arcuate --.

In Column 4, Line 56, delete "arcurate" and insert -- arcuate --.

In Column 6, Line 23, delete "arcurate" and insert -- arcuate --.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,433,469 B2

In Column 6, Line 41, delete "arcurate" and insert -- arcuate --.

In Column 6, Line 52, delete "arcurate" and insert -- arcuate --.

In Column 7, Line 30, delete "arcurate" and insert -- arcuate --.

In Column 7, Line 33, delete "arcurate" and insert -- arcuate --.

In Column 8, Line 41, delete "arcurate" and insert -- arcuate --.

In Column 8, Line 42, delete "arcurate" and insert -- arcuate --.

In Column 8, Line 59, delete "arcurate" and insert -- arcuate --.

In Column 9, Line 13, delete "arcurate" and insert -- arcuate --.

In Column 9, Line 44, delete "arcurate" and insert -- arcuate --.

In Column 9, Line 52, delete "arcurate" and insert -- arcuate --.

In Column 9, Line 58, delete "arcurate" and insert -- arcuate --.

In Column 10, Line 11, delete "arcurate walls" and insert -- arcuate walls --.

In Column 10, Line 12, delete "arcurate wall" and insert -- arcuate wall --.

In Column 10, Line 27, delete "arcurate" and insert -- arcuate --.

In Column 10, Line 33, delete "arcurate" and insert -- arcuate --.

In Column 10, Line 35, delete "arcurate" and insert -- arcuate --.

In Column 10, Line 45, delete "arcurate" and insert -- arcuate --.

In Column 10, Line 47, delete "arcurate" and insert -- arcuate --.

In Column 10, Line 57, delete "arcurate" and insert -- arcuate --.

In Column 12, Line 4, delete "arcurate" and insert -- arcuate --.

In the Claims

In Column 12, Line 37, in Claim 1, after "said" delete "second".
In Column 12, Line 62, in Claim 4, after "having" delete ";" and insert -- : --.

CERTIFICATE OF CORRECTION (continued)
U.S. Pat. No. 9,433,469 B2

In Column 13, Line 20, in Claim 5, delete "Wherein" and insert -- wherein --.

In Column 14, Line 22, in Claim 14, after "having" delete ";" and insert -- : --.

In Column 15, Line 12, in Claim 21, after "tray" insert -- and --.

In Column 15, Line 19-20, in Claim 22, delete "opposites" and insert -- opposite --.